United States Patent
Fallis

(10) Patent No.: US 8,603,056 B1
(45) Date of Patent: Dec. 10, 2013

(54) PORTABLE FEMALE URINAL

(71) Applicant: Martha Jane Smith Fallis, Clearwater, FL (US)

(72) Inventor: Martha Jane Smith Fallis, Clearwater, FL (US)

( * ) Notice: Subject to any disclaimer, the term of this patent is extended or adjusted under 35 U.S.C. 154(b) by 0 days.

(21) Appl. No.: 13/742,926

(22) Filed: Jan. 16, 2013

(51) Int. Cl.
*A61M 1/00* (2006.01)

(52) U.S. Cl.
USPC ........................................................ 604/318

(58) Field of Classification Search
USPC ........................................................ 604/318
See application file for complete search history.

(56) References Cited

U.S. PATENT DOCUMENTS

| | | | | |
|---|---|---|---|---|
| 3,194,238 A * | 7/1965 | Breece, Jr. | | 604/329 |
| 3,548,827 A * | 12/1970 | Abel | | 604/318 |
| 3,699,964 A * | 10/1972 | Ericson | | 604/33 |
| 3,762,399 A * | 10/1973 | Riedell | | 600/580 |
| 3,776,235 A * | 12/1973 | Ratcliffe et al. | | 604/329 |
| 3,888,235 A * | 6/1975 | May et al. | | 600/574 |
| 3,995,329 A * | 12/1976 | Williams | | 4/144.3 |
| 4,198,979 A * | 4/1980 | Cooney et al. | | 604/329 |
| 4,204,527 A * | 5/1980 | Wu et al. | | 600/575 |
| 4,246,901 A * | 1/1981 | Frosch et al. | | 604/329 |
| 4,281,655 A * | 8/1981 | Terauchi | | 604/73 |
| 4,484,917 A * | 11/1984 | Blackmon | | 604/327 |
| 4,496,355 A * | 1/1985 | Hall et al. | | 604/327 |
| 4,568,339 A * | 2/1986 | Steer | | 604/329 |
| 4,569,090 A * | 2/1986 | Muller | | 4/144.2 |
| 4,681,572 A * | 7/1987 | Tokarz et al. | | 604/329 |
| 4,690,677 A * | 9/1987 | Erb | | 604/329 |
| 4,753,249 A * | 6/1988 | Muller | | 600/584 |
| 4,764,991 A * | 8/1988 | Saleme | | 4/144.1 |
| 4,795,449 A * | 1/1989 | Schneider et al. | | 604/329 |
| 4,889,532 A * | 12/1989 | Metz et al. | | 604/330 |
| 4,889,533 A * | 12/1989 | Beecher | | 604/330 |
| 4,904,248 A * | 2/1990 | Vaillancourt | | 604/329 |
| 4,986,823 A * | 1/1991 | Anderson et al. | | 604/329 |
| 5,053,027 A * | 10/1991 | Manfredi | | 604/327 |
| 5,336,208 A * | 8/1994 | Rosenbluth et al. | | 604/329 |
| 5,411,495 A * | 5/1995 | Willingham | | 604/329 |
| 5,655,229 A * | 8/1997 | Horn | | 4/144.3 |
| 5,735,835 A * | 4/1998 | Holland | | 604/331 |
| 6,302,303 B1 * | 10/2001 | Reynolds | | 222/175 |
| 6,342,049 B1 * | 1/2002 | Nichols | | 604/329 |
| D467,338 S * | 12/2002 | Rehrig | | D24/122 |
| 6,592,560 B2 * | 7/2003 | Snyder | | 604/331 |
| 6,635,797 B2 * | 10/2003 | Olson et al. | | 604/361 |
| 6,684,414 B1 * | 2/2004 | Rehrig | | 4/144.1 |
| 6,702,793 B1 * | 3/2004 | Sweetser | | 604/327 |
| 7,875,010 B2 * | 1/2011 | Frazier et al. | | 604/329 |
| 7,993,312 B2 * | 8/2011 | Mahalingam | | 604/329 |
| 2002/0087131 A1 * | 7/2002 | Wolff et al. | | 604/319 |
| 2002/0193760 A1 * | 12/2002 | Thompson | | 604/318 |
| 2005/0097662 A1 * | 5/2005 | Leimkuhler | | 4/144.3 |
| 2006/0111681 A1 * | 5/2006 | Vernon | | 604/326 |
| 2009/0048569 A1 * | 2/2009 | Salehi | | 604/347 |
| 2011/0172620 A1 * | 7/2011 | Khambatta | | 604/347 |

\* cited by examiner

*Primary Examiner* — Tatyana Zalukaeva
*Assistant Examiner* — Guy K Townsend

(57) ABSTRACT

A urinal has a closed bottom and an open top. The urinal has a peripheral wall. The urinal has an outlet cylinder. The peripheral wall has a peripheral edge at the open top. A covering is provided at the peripheral edge. The urinal is positionable laterally intra-labially underlying the labia majora and overlying or contacting the labia minora to cover a user's genitalia to allow the collection of urine.

9 Claims, 4 Drawing Sheets

FIG. 2
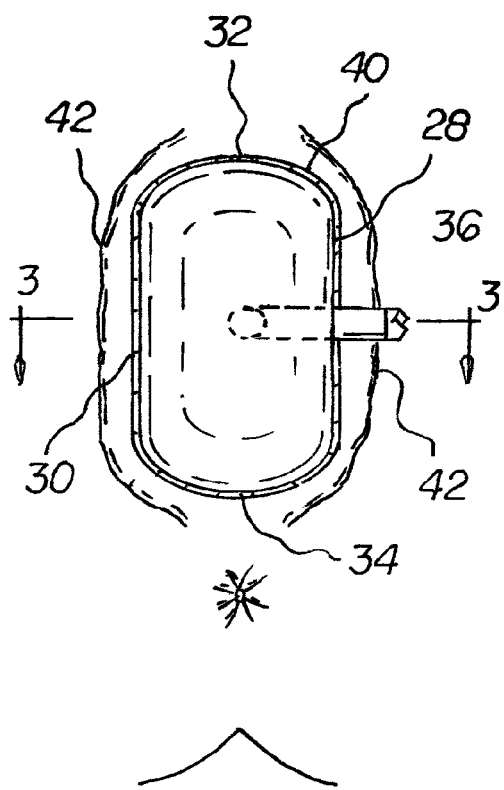
FIG. 3
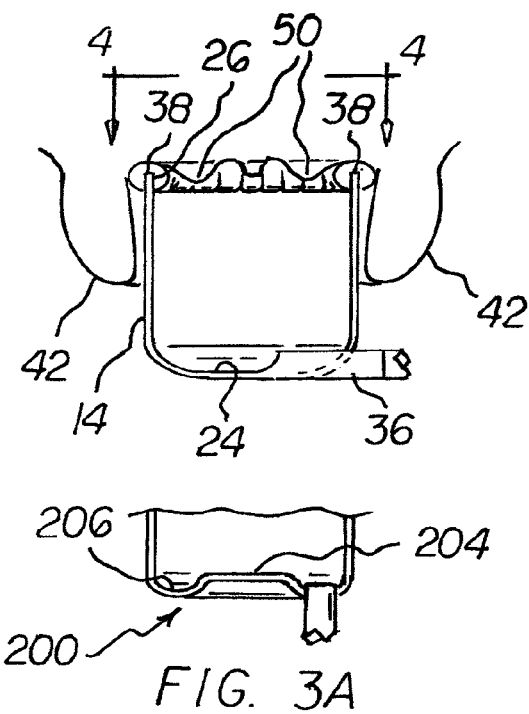
FIG. 3A
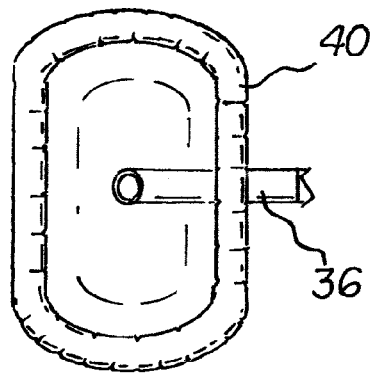
FIG. 4

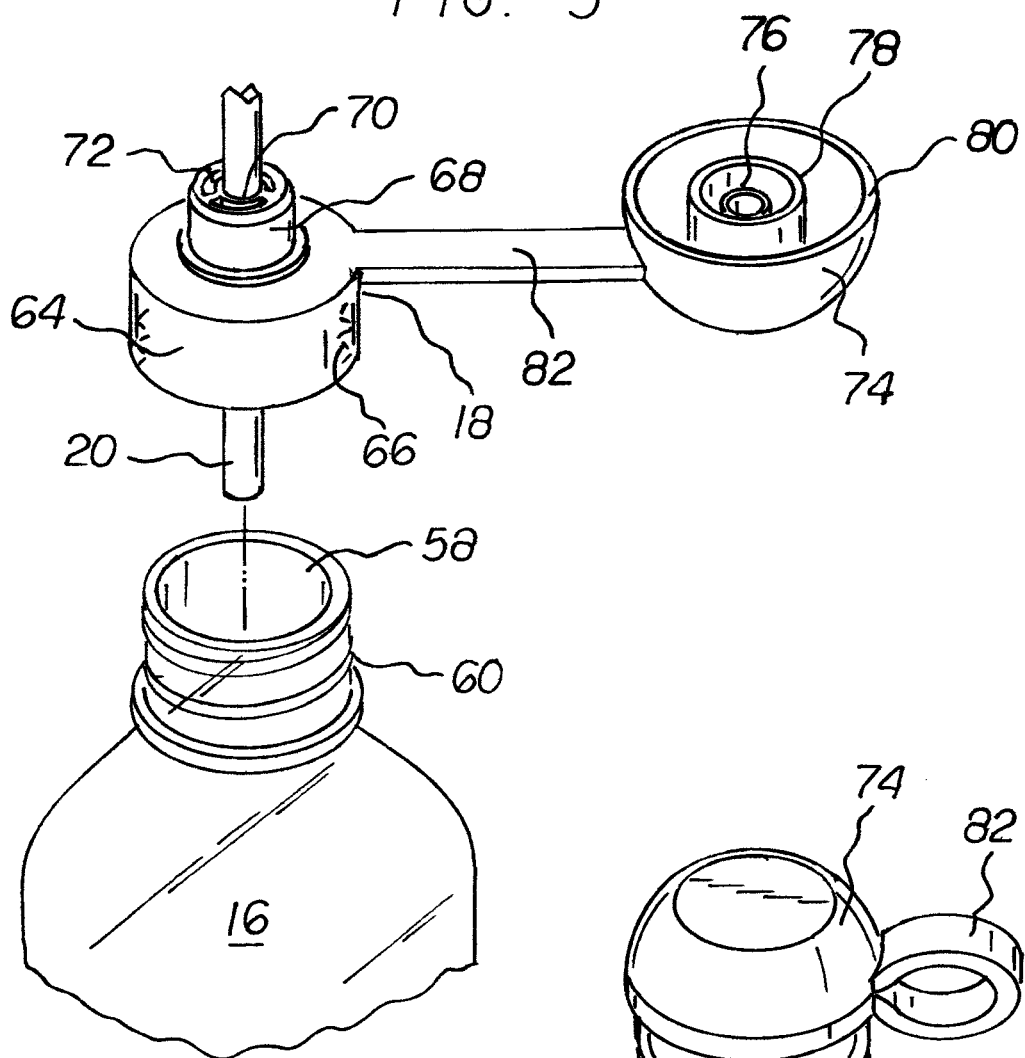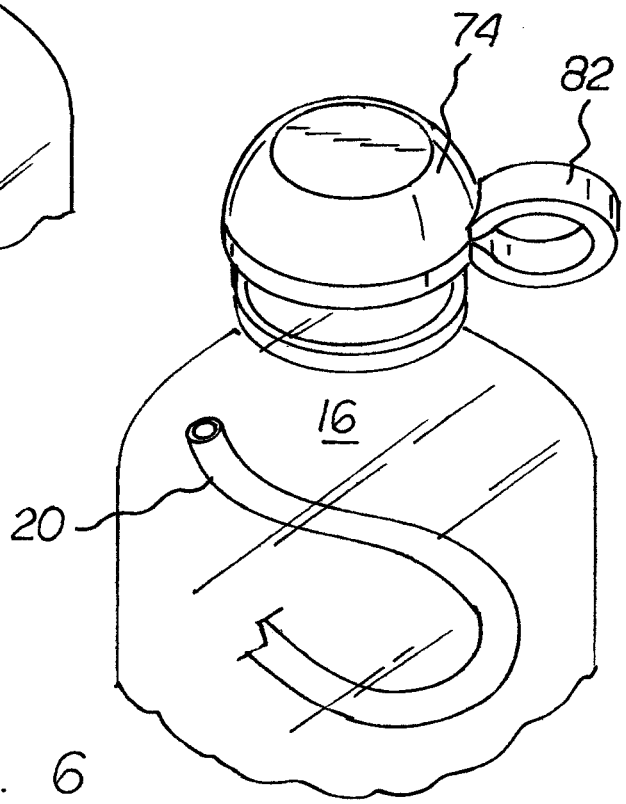

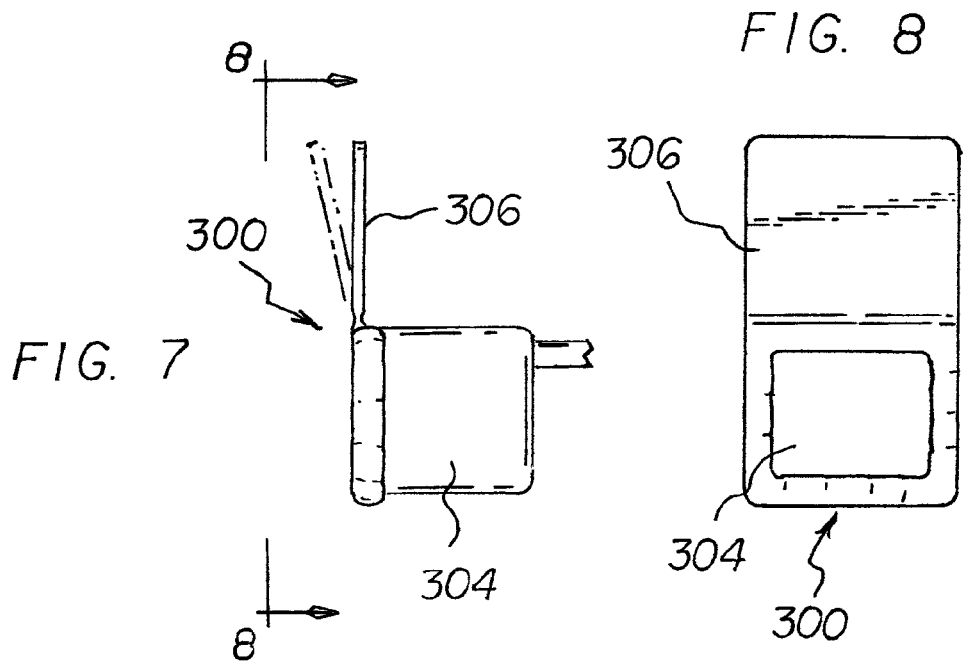
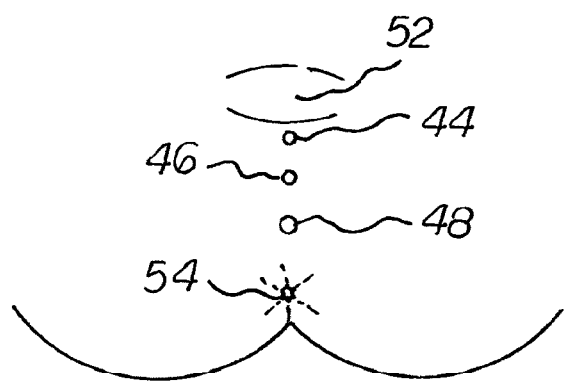

PORTABLE FEMALE URINAL

BACKGROUND OF THE INVENTION

Field of the Invention

The present invention relates to a portable female urinal and more particularly pertains to facilitating intra-labial positioning and urine collecting, the positioning and collecting being done in a sanitary, safe, discreet, convenient and economical manner.

SUMMARY OF THE INVENTION

In view of the disadvantages inherent in the known types of urinals now present in the prior art, the present invention provides an improved portable female urinal. As such, the general purpose of the present invention, which will be described subsequently in greater detail, is to provide a new and improved portable female urinal and method which has all the advantages of the prior art and none of the disadvantages.

To attain this, the present invention essentially comprises a portable female urinal. A urinal has a closed bottom and an open top. The urinal has a peripheral wall. The urinal has an outlet cylinder. The peripheral wall has a peripheral edge at the open top. A covering is provided at the peripheral edge. The urinal is positionable laterally intra-labially within the labia majora to cover a user's genitalia.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved portable female urinal which has all of the advantages of the prior art urinals and none of the disadvantages.

It is another object of the present invention to provide a new and improved portable female urinal which may be easily and efficiently manufactured and marketed.

It is further object of the present invention to provide a new and improved portable female urinal which is of durable and reliable constructions.

An even further object of the present invention is to provide a new and improved portable female urinal which is susceptible of a low cost of manufacture with regard to both materials and labor, and which accordingly is then susceptible of low prices of sale to the consuming public, thereby making such portable female urinal economically available to the buying public.

Lastly, it is an object of the present invention to provide a new and improved portable female urinal for facilitating intra-labial positioning and urine collecting, the positioning being within the labia majora allowing the collecting to be done in a sanitary, safe, discreet, convenient and economical manner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a cross sectional view taken along line 2-2 of FIG. 1.

FIG. 3 is a cross sectional view taken along line 3-3 of FIG. 2.

FIG. 3A is a cross sectional view similar to FIG. 3 but illustrating an alternate embodiment of the invention.

FIG. 4 is a front elevational view taken along line 4-4 of FIG. 3.

FIG. 5 is a perspective illustration of the hinge and portions of the tube and container shown in the prior Figures prior to and during use.

FIG. 6 is a perspective illustration similar to FIG. 5 but shown after use.

FIG. 7 is a side elevational view of an alternate embodiment of the invention.

FIG. 8 is a front elevational view of the alternate embodiment of the invention shown in FIG. 7.

FIG. 9 shows the area of the female anatomy where the urinal of the present invention is received.

The same reference numerals refer to the same parts throughout the various Figures.

DESCRIPTION OF THE PREFERRED EMBODIMENT

Figure 1:
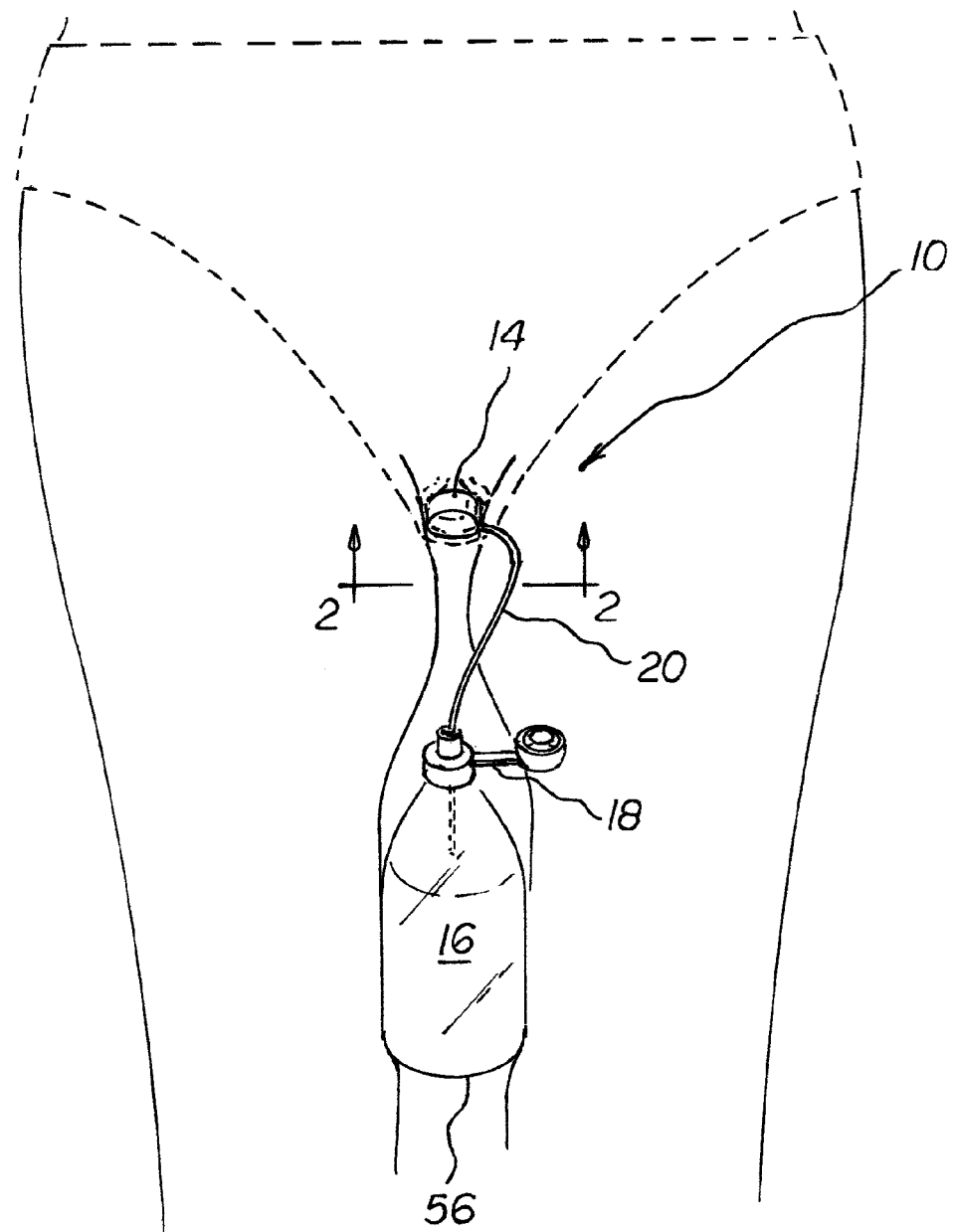
FIG. 1 is a front elevational view of a portable female urinal constructed in accordance with the principles of the present invention.

With reference now to the drawings, and in particular to FIG. 1 thereof, the preferred embodiment of the new and improved portable female urinal embodying the principles and concepts of the present invention and generally designated by the reference numeral 10 will be described.

The present invention is a portable female urinal 10. First provided is an intra-labial urinal 14. A container 16 is provided. A container closure 18 is also provided. Further provided is a tube 20.

The intra-labial urinal has a generally rectilinear configuration with a planar closed bottom 24 and a parallel open top 26. The closed bottom and open top are separated by a depth of 2.0 centimeters plus or minus 10 percent. The intra-labial urinal has a left side wall 28 and a parallel right side wall 30. The left side wall and the right side wall are separated by a width of 2.0 centimeters plus or minus 10 percent. The intra-labial urinal has a front wall 32 and a rear wall 34. The front and rear walls are separated by a length of 3.0 centimeters plus or minus 10 percent. The intra-labial urinal has an outlet cylinder 36. In the preferred embodiment the outlet cylinder extends from one side wall adjacent to the bottom. In other embodiments, the outlet cylinder may extend from other locations including from the closed bottom. The bottom and side walls and front and rear walls are fabricated of a generally rigid plastic material with limited flexibility. The side walls and front and rear walls form a peripheral edge 38 at the open top. A covering 40 is provided at the peripheral edge. In the preferred embodiment, the covering is a soft pliable air-filled chamber 40. In alternate embodiments, the covering is selected from a group of coverings including an air-filled tube, a rolled edge, foam, and a wide variety of other materials. The intra-labial urinal is laterally positionable intra-labially within the labia majora 42 to cover a user's genitalia including the clitoris 44 and urethral orifice 46 and vagina 48. The positioning is within the labia majora with the chamber adjacent to the front wall overlying or within the labia minora 50 and the rigid pubic symphysis 52. The positioning is also with the chamber adjacent to the rear and side walls overlying soft tissue adjacent to the labia majora and anus 54. The positioning may be varied depending upon unique variations in female anatomy.

The container 16 has a closed base 56, an upper opening 58, and a periphery. The upper opening has male threads 60. The container is adapted to be supported between the thighs of the user during use. The container is fabricated of a generally rigid material, the preferred material being a plastic. The container is adapted to receive urine from the intra-labial urinal. Preferably, the material for the container is a thermochromic which will change color when in contact with warm human urine to indicate prior usage of the container. Alternatively, a wide variety of other materials including recyclable organic materials, bamboo, paper, and stainless steel, may be used.

Further provided is a cylindrically-shaped component 64. The container closure has female threads 66. The female threads are removably received on the male threads of the container. The cylindrically-shaped component has a raised central section 68. The cylindrically-shaped component has a central passageway 70. The cylindrically-shaped component has air exit vent holes 72. The container closure has a dome-shaped component 74. The dome-shaped component has an interior sealing ring 76. The interior sealing ring is positionable on the raised central section. The dome-shape component also has an intermediate sealing ring 78. The intermediate sealing ring is positionable on the cylindrically-shaped component adjacent to the raised central section. The dome-shaped component also has an exterior sealing ring 80. The exterior sealing ring is positionable on the cylindrically-shaped component remote from the raised central section. The container closure has a living hinge 82. The living hinge couples the cylindrically-shaped component and the dome-shaped component. The dome-shaped component is spaced from the cylindrically-shaped component prior to and during use. The dome-shaped component covers the cylindrically-shaped component after use. The container closure is preferably fabricated of a plastic material. It should be understood that the container closure could be fabricated of a wide variety of other materials in alternate embodiments of the invention.

Provided last is a flexible tube 86. The flexible tube has an upper end. The upper end is received on the outlet cylinder of the intra-labial urinal. The flexible tube has a lower end. The lower end is positionable in the container. The flexible tube has an intermediate extent. The intermediate extent is positionable through the central passageway of the container closure during use. The entire flexible tube is positioned within the container after use with the dome-shaped component positioned in a leakproof manner over the cylindrically-shaped component and the container.

An alternate embodiment 200 of the present invention is shown in FIG. 3A. In the alternate embodiment the bottom of the urinal has a planar central section 204 and a recessed periphery 206.

Another alternate embodiment of the present invention 300 is shown in FIGS. 7 and 8. In this embodiment, the urinal 304 has a length of less than 3 centimeters. In this embodiment the urinal is laterally positionable to cover the user's genitalia including clitoris and urethral orifice. In this embodiment, the urinal has a front wall positionable overlying the labia minora and the rigid pubic symphysis of the user. Also, the urinal has rear and side walls positionable overlying soft tissue adjacent to the labia majora. In this embodiment, a rectangular lid 306 is provided. The rectangular lid is pivotally coupled to the urinal to facilitate holding the system during use and to allow closing after use.

It should be understood that the container or multiple containers may be filled, sealed, and collected for disposal or use at a later time and/or location. Use of urine in the generation of electricity is the subject of current experimentation.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A portable urinal system consisting essentially of:
a urinal having a bottom and an open top, the urinal having a peripheral wall, the urinal having an outlet cylinder, the peripheral wall formed with a peripheral edge at the open top, a covering at the peripheral edge, the urinal having a left side wall and a right side wall separated by a width, the urinal having a front wall and a rear wall separated by a length, the urinal having an outlet cylinder extending from one side wall adjacent to the bottom, the bottom and side walls and front and rear walls forming a chamber and being fabricated of a generally rigid plastic material with limited flexibility, the side walls and front and rear walls forming the peripheral edge at the open top, the peripheral edge of the open top of side walls of the urinal being laterally positionable intra-labially between the labia majora to cover a user's genitalia including the user's clitoris and urethral orifice, with the chamber adjacent to the front wall overlying the user's rigid pubic symphysis and with the chamber adjacent to the rear and side walls overlying soft tissue adjacent to the labia majora and anus, the portable urinal system being held in place during use solely supportable between the thighs of the user during use by the user;

a container having an upper opening and a periphery; and a flexible tube with an upper end received on the outlet cylinder of the urinal, the flexible tube having a lower end positionable in the container, the flexible tube having an intermediate extent positionable through the central passageway of the container closure during use;

wherein the container has a closed base and an upper opening and a periphery, the upper opening having male threads, the container adapted to be supported between the thighs of the user during use, the container being fabricated of a generally rigid plastic material and adapted to receive urine from the intra-labial urinal;

the container closure having a cylindrically-shaped component with female threads removably received on the male threads of the container, the cylindrically-shaped component having a raised central section with a central passageway and air exit vent holes, the container closure having a dome-shaped component, the dome-shaped component having an interior sealing ring positionable on the raised central section, the dome-shape component also having an intermediate sealing ring positionable on the cylindrically-shaped component adjacent to the raised central section, the dome-shaped component also having an exterior sealing ring positionable on the cylindrically-shaped component remote from the raised central section, the container closure having a living hinge coupling the cylindrically-shaped component and the dome-shaped component, the dome-shaped component being spaced from the cylindrically-shaped component prior to and during use, the dome-shaped component covering the cylindrically-shaped component after use, the container closure being fabricated of a plastic material; and the flexible tube having an upper end received on the outlet cylinder of the intra-labial urinal, the flexible tube having a lower end positionable in the container, the flexible tube having an intermediate extent positionable through the central passageway of the container closure during use, the entire flexible tube positioned within the container after use with the dome-shaped component positioned in a leakproof manner over the cylindrically-shaped component and the container.

2. The system as set forth in claim 1 wherein the covering at the peripheral edge is selected from a group of coverings including an air-filled tube, a rolled edge and foam.

3. The system as set forth in claim 1 wherein the urinal is fabricated of a plastic material.

4. The system as set forth in claim 1 the container further including an opening in the bottom to a drain.

5. The system as set forth in claim 4 wherein the container is fabricated of a thermochromic material to indicate prior usage.

6. The system as set forth in claim 1 wherein the bottom of the urinal is planar.

7. The system (200) as set forth in claim 1 wherein the bottom of the urinal has a planar central section (204) and a recessed periphery (206).

8. The system (300) as set forth in claim 1 wherein the urinal (304) includes a lid (306) pivotally coupled the urinal to facilitate holding the system during use and to allow closing after use.

9. A female portable urinal system (10) for facilitating intra-labial positioning and urine collecting, the positioning and collecting being done in a sanitary, safe, discreet, convenient and economical manner, the system consisting essentially of, in combination:

an intra-labial urinal (14), a container (16), a container closure (18) and a tube (20);

the intra-labial urinal having a generally rectilinear configuration with a planar an opening in the bottom to the drain and a parallel open top (26) separated by a depth of 2.0 centimeters plus or minus 10 percent, the intra-labial urinal having a left side wall (28) and a parallel right side wall (30) separated by a width of 2.0 centimeters plus or minus 10 percent, the intra-labial urinal having a front wall (32) and a rear wall (34) separated by a length of 3.0 centimeters plus or minus 10 percent, the intra-labial urinal having an outlet cylinder (36) extending from one side wall adjacent to the bottom, the bottom and side walls and front and rear walls being fabricated of a generally rigid plastic material with limited flexibility, the side walls and front and rear walls forming a peripheral edge (38) at the open top, a soft pliable air-filled chamber (40) covering the peripheral edge, the peripheral edge of the open top of the side walls of the intra-labial urinal being laterally positionable intra-labially between the labia majora; (42) to cover a user's genitalia including clitoris (44) and urethral orifice (46), with the chamber adjacent to the front wall overlying the labia minora (50) and the rigid pubic symphysis (52) and with the chamber adjacent to the rear and side walls overlying soft tissue adjacent to the labia majora and anus (54);

the portable urinal system being held in place during use solely supportable between the thighs of the user during use by the user;

the container having a closed base (56) and an upper opening (58) and a periphery, the upper opening having male threads (60), the container adapted to be supported between the thighs of the user during use, the container being fabricated of a generally rigid plastic material and adapted to receive urine from the intra-labial urinal, the container being fabricated of a thermochromic material which will change color when in contact with warm human urine to indicate prior usage;

the container closure having a cylindrically-shaped component (64) with female threads (66) removably received on the male threads of the container, the cylindrically-shaped component having a raised central section (68) with a central passageway (70) and air exit vent holes (72), the container closure having a dome-shaped component (74), the dome-shaped component having an interior sealing ring (76) positionable on the raised central section, the dome-shape component also have an intermediate sealing ring (78) positionable on the cylindrically-shaped component adjacent to the raised central section, the dome-shaped component also having an exterior sealing ring (80) positionable on the cylindrically-shaped component remote from the raised central section, the container closure having a living hinge (82) coupling the cylindrically-shaped component and the dome-shaped component, the dome-shaped component being spaced from the cylindrically-shaped component prior to and during use, the dome-shaped component covering the cylindrically-shaped component after use, the container closure being fabricated of a plastic material; and the flexible tube (86) having an upper end received on the outlet cylinder of the intra-labial urinal, the flexible tube having a lower end positionable in the container, the flexible tube having an intermediate extent positionable through the central passageway of the container closure during use, the entire flexible tube positioned within the container after use with the dome-shaped component positioned in a leakproof manner over the cylindrically-shaped component and the container.

\* \* \* \* \*